United States Patent [19]

Theisler

[11] 4,240,414
[45] Dec. 23, 1980

[54] KNEE BRACE

[76] Inventor: Charles W. Theisler, 1749 S. Raccoon Rd., Youngstown, Ohio 44515

[21] Appl. No.: 65,220

[22] Filed: Aug. 9, 1979

[51] Int. Cl.³ ............................................... A61F 3/00
[52] U.S. Cl. .................................................. 128/80 C
[58] Field of Search .................... 128/80 C, 80 R, 87, 128/165; 2/22, 24

[56] References Cited

U.S. PATENT DOCUMENTS

| | | | |
|---|---|---|---|
| 3,046,981 | 7/1962 | Biggs, Jr. et al. ................. | 128/80 C |
| 3,387,305 | 6/1968 | Shafer ................................ | 128/80 C |
| 3,669,105 | 6/1972 | Castiglia ............................ | 128/80 C |
| 3,934,583 | 1/1976 | Hollingshead et al. ............. | 128/165 |
| 3,945,046 | 3/1976 | Stromgren ......................... | 128/80 C |

Primary Examiner—John D. Yasko
Attorney, Agent, or Firm—Webster B. Harpman

[57] ABSTRACT

A knee brace designed to help stabilize the knee ligaments and provide support for the knee joint, comprises a tubular elastic sheath placed over the knee, a strap attached midway between its ends to the sheath which wraps around the sheath and crosses behind the knee cap in a crisscross manner to achieve the added support of the knee ligaments. The knee brace contains no supportive rigid components and does not impede normal flexability of the knee joint. An apertured disc is positioned on the sheath by the strap which applies pressure on it to relieve the pain associated with Osgood-Schlaughter disease.

4 Claims, 4 Drawing Figures

KNEE BRACE

BACKGROUND OF THE INVENTION (1) Field of the Invention

This invention relates to knee supports of the type used to protect the knee from injury and additionally support the knee ligaments.

(2) Description of the Prior Art

Prior devices of this type have used a variety of supportive means both rigid and flexible. See for example U.S. Pat. Nos. 1,622,211; 3,463,147 and 3,945,046.

In U.S. Pat. No. 1,622,211 a knee brace is disclosed having a pair of spaced elastic bands with support straps holding the same in place on the knee.

In applicant's device a single elastic sheath is used in connection with a single support strap and the combination covers the entire knee joint area.

In U.S. Pat. No. 3,463,147 a body joint support is shown having multiple layers consisting of a cushion pad, a flexible outer covering, a knee cap covering and a pair of support straps.

Applicant's invention relies on a single elastic sheath and a single crossed supportive strap covering the knee joint in a crisscross sprial manner.

In U.S. Pat. No. 3,945,046 a flexible knee support is shown having a tubular elastic band, a pair of felt pads and a pair of elastic straps which are placed over the knee joint for support.

Applicant's device uses an elastic tubular sheath and one flexible strap and locates an apertured disc or donut-shaped member so that it will relieve the pain associated with Osgood-Schlaughter disease.

SUMMARY OF THE INVENTION

A knee brace comprising an elastic tubular sheath is placed over the knee joint. A single non-flexible strap attached midway between its ends to the lower front portion of the sheath has its ends spirally wrapped over the sheath in a crisscross fashion and fastened, thus stabilizing the knee ligaments. A donut-shaped disc is located by the strap to relieve pain associates with the Osgood-Schlaughter disease. The strap provides adjustable tension above and below the knee joint.

DESCRIPTION OF THE PREFERRED EMBODIMENT

Figure 1:
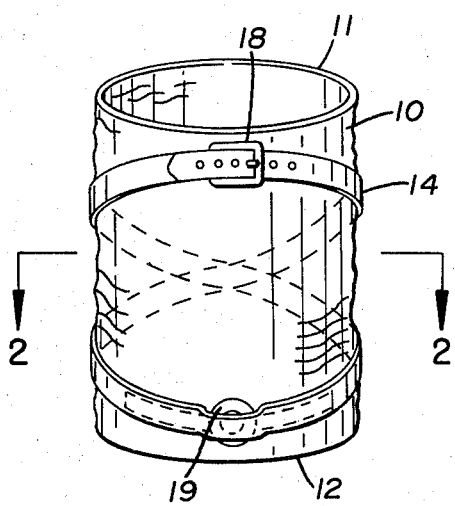
FIG. 1 is a front elevation of the knee brace.
Figure 2:
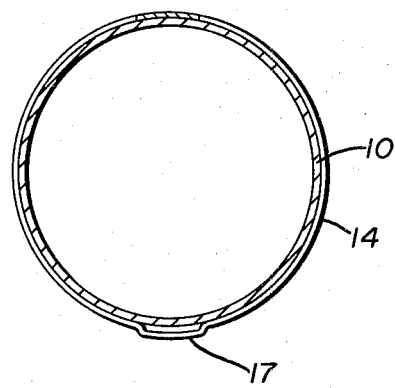
FIG. 2 is a section on line 2—2 of FIG. 1.
Figure 3:
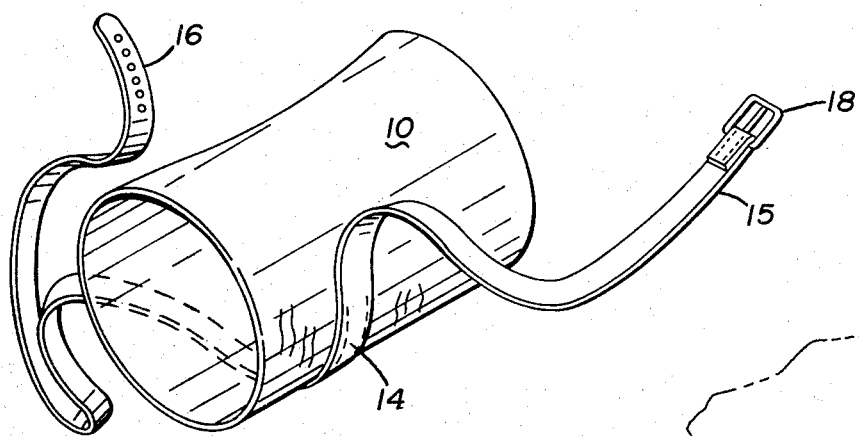
FIG. 3 is a perspective view of the knee brace.
Figure 4:
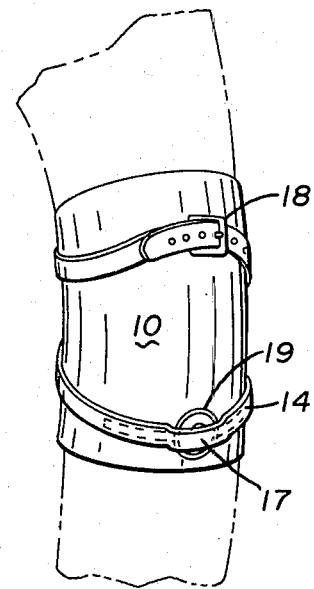
FIG. 4 is a perspective view of the knee brace in position on the wearer's leg.

The knee brace as seen in FIGS. 1, 2 and 3 of the drawings comprises an elastic tubular sheath 10 having an upper end 11 and a lower end 12. The sheath 10 is shown as having the cylindrical form it takes when placed on a person's leg covering the knee joint and knee cap as seen in FIG. 4 of the drawings. A single non-elastic strap 14 having ends 15 and 16 is secured midway between its ends to the lower front portion of the sheath 10 at a point inwardly of the lower end 12 and below the knee cap as by sewing or other suitable means so as to form two free portions. A pocket 17 is formed in the strap 14 or the sheath 10, preferably by the attachment of the strap 14 to the sheath 10. A donut-shaped disc 19 is positioned in the pocket.

Referring now to FIGS. 1 and 4 of the drawings, the strap 14 will be seen to be wrapped in a spiral crisscross fashion around the sheath 10 and knee of the wearer so as to freely cross at the back of the knee joint at a point midway between the upper end 11 and the lower end 12 of the sheath. The ends 15 and 16 of the free portions of the strap 14 are secured to one another by a fastener 18 such as an adjustable buckle and are freely located at the upper front portion of said sheath above the knee cap.

It will thus be seen that due to the non-elastic qualities of the strap 14 a controlled tension may be realized. The donut-shaped disc 19 is formed of semi-rigid material and when located in the pocket 17 formed by the strap 14, the disc 19 provides controlled pressure on the bone structure just below the knee joint where it relieves the pain associated with the softening of the bone as caused by the Osgood-Schlaughter disease. In utilizing the knee brace additional controlled support is provided by the sheath 10 when it is pulled on the leg by the user and positioned properly over the knee joint with the knee cap midway between the upper and lower ends 11 and 12 of the sheath 10.

The device of the invention when properly located maintains its location as the ends of the two portions of the strap 14 are wrapped about the knee and fastened by the fastener 18. The fastener 18 and the midpoint of the strap are thus spaced above and below the knee cap which provides the desired flexibility and freedom of motion while supporting the ligaments associated with the knee joint.

The somewhat radially extended condition of the sheath 10 helps maintain the device on the knee and in itself provides some support to the knee joint and the ligaments thereabout. The strap 14 by its spiral crisscross nature provides the additional support needed by passing under the knee joint as well as passing over and around it.

Accordingly the strap follows the direction of the knee ligaments and applies laterally outwardly directed pressure to the knee region from the inside of the leg. Being located as described above, the strap 11 reduces the chance of medial knee ligament instability and any external tibial rotary instability. The rotary instability referred to comprises the action of the foot in swinging in one direction without any corresponding movement in the knee. The flexibility of the knee joint is thus assured while providing constant alignment and support to the knee joint and the ligaments associated therewith.

Although but one embodiment of the present invention has been illustrated and described, it will be apparent to those skilled in the art that various changes and modifications may be made therein without departing from the spirit of the invention and having thus described my invention what I claim is:

1. A knee brace comprising an elastic tubular sheath of a length to cover the knee joint and knee cap and knee ligaments when positioned on a wearer's knee, a single non-elastic strap secured at a point midway between its ends to said sheath in a lower front portion thereof below the knee cap so as to form two free portions, fastening means attached to the ends of the free portions for securing the ends of the free portions of the strap to one another at the upper front portion of the sheath above the knee cap, the free portions of the strap being arranged to be wrapped in opposed spiral patterns around the sheath in a crisscross manner crossing behind the knee joint, a pocket formed between said strap and said sheath at the point of attachment of said strap to said sheath, a donut shaped semi-rigid disc positioned in said pocket so that said strap tensions said disc relative to said wearer.

2. The knee brace of claim 1 wherein said fastening means for securing the free end portions of the strap to one another comprises an adjustable fastening device.

3. The knee brace of claim 1 and wherein the tubular elastic sheath is of a known diameter and the strap is of a length sufficient to permit each free portion thereof to be wrapped around the sheath at least once.

4. The knee brace of claim 1 and wherein the fastening means comprises a buckle on one end of said strap having a movable member engagable in one of a plurality of openings in the other end of said strap.

* * * * *